(12) United States Patent
Iwasa et al.

(10) Patent No.: US 6,602,647 B2
(45) Date of Patent: Aug. 5, 2003

(54) SULFONIUM SALT COMPOUND AND RESIST COMPOSITION AND PATTERN FORMING METHOD USING THE SAME

(75) Inventors: Shigeyuki Iwasa, Tokyo (JP); Katsumi Maeda, Tokyo (JP); Kaichiro Nakano, Tokyo (JP); Etsuo Hasegawa, Tokyo (JP)

(73) Assignee: NEC Corporation, Tokyo (JP)

( * ) Notice: Subject to any disclaimer, the term of this patent is extended or adjusted under 35 U.S.C. 154(b) by 64 days.

(21) Appl. No.: 09/734,563

(22) Filed: Dec. 13, 2000

(65) Prior Publication Data

US 2002/0045122 A1 Apr. 18, 2002

(30) Foreign Application Priority Data

| Dec. 28, 1999 | (JP) | ............................................. | 11-377299 |
| Apr. 14, 2000 | (JP) | ........................................ | 2000-114125 |
| Dec. 5, 2000 | (JP) | ........................................ | 2000-369872 |

(51) Int. Cl.[7] ............................................... G03F 7/004
(52) U.S. Cl. .................................... 430/270.1; 430/922
(58) Field of Search ............................... 430/270.1, 922

(56) References Cited

U.S. PATENT DOCUMENTS 5,756,850 A  5/1998  Iwasa et al.

FOREIGN PATENT DOCUMENTS

| EP | 0-877293 A2 | 11/1998 |
| EP | 0-877293 A3 | 6/1999 |
| JP | 56-152833 | * 11/1981 |
| JP | A 56-152833 | 11/1981 |
| JP | 2578646 | 11/1996 |
| JP | 2776204 | 5/1998 |
| JP | 11-133607 | 5/1999 |
| JP | 2964990 | 8/1999 |
| JP | 2965016 | 8/1999 |
| JP | 11-228534 | 8/1999 |

OTHER PUBLICATIONS

Chemical Abstracts AN 1977:72327.*
Chemical Abstracts AN 1971:12542.*
Chemical Abstracts AN 1985:166556.*
Chemical Abstracts AN 1983:612394.*
Chemical Abstracts AN 1993:147443.*
Chemical Abstracts AN 1988:150552.*

Mitsuaki Watanabe et al., "Stable Sulfur Ylides. V.[1)] Syntheses of α–Acylfuran Derivatives by Thermal and Photochemical Reaction of Allylides," Chem. Pharm. Bull, V. 24, 1976, pp. 2421–2427.

V.E. Krivenchuk, "Oximes of dialkyl– and alkyleneacetonyl–sulfonium bromides", p. 264, col. 1, Chemical Abstracts, vol. 74, No. 3, abstract No. 12542, Jan. 18, 1971, Columbus OH.

M. Watanabe etal., "Stable sulfur ylides", p. 584, col. 2, Chenical Abstracts, vol. 86, No. 11, abstract No. 72327, Mar. 14, 1977, Columbus, OH.

*Khim. Farm. Zh.*, V. 4, 1970, p. 18–22.

* cited by examiner

Primary Examiner—Rosemary Ashton
(74) Attorney, Agent, or Firm—Young & Thompson

(57) ABSTRACT

The present invention relates to a photo acid generator which has high transparency to exposure light and also has excellent heat stability in a photoresist composition for lithography using far ultraviolet light, especially light of ArF excimer laser. The photo acid generator contains a sulfonium salt compound represented by the following general formula (1):

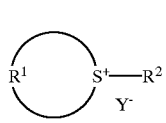

(1)

wherein $R^1$ represents an alkylene group, or an alkylene group having an oxo group, $R^2$ represents a straight-chain, branched-chain, monocyclic, polycyclic or bridged cyclic alkyl group having an oxo group, or a straight-chain, branched-chain, monocyclic, polycyclic or bridged cyclic alkyl group, provided that either of $R^1$ and $R^2$ has an oxo group, and $Y^-$ represents a counter ion.

14 Claims, 1 Drawing Sheet

SULFONIUM SALT COMPOUND AND RESIST COMPOSITION AND PATTERN FORMING METHOD USING THE SAME

BACKGROUND OF THE INVENTION

1. Field of the Invention

The present invention relates to a sulfonium salt compound suited for use as a photo acid generator of a resist for lithography using far ultraviolet light, especially light of an ArF excimer laser, as exposure light, a photoresist composition, and a pattern forming method using the same.

2. Description of Prior Art

Higher density and higher integration of various semiconductor devices, which require a precision-precise working at a half-micron order, have been advanced conventionally. Therefore, requirements for the lithographic technology for formation of a precision circuit pattern have been more enhanced.

A means for refining a pattern is to use a lithographic light source having a shorter wavelength. Therefore, a KrF excimer laser having a shorter wavelength (wavelength=248 nm) is now employed in place of a conventional i-ray (wavelength=365 nm) in the mass production process of DRAM having an integration degree within a range of 256 Mbit to 1 Gbit (working size is within a range of 0.25–0.15 $\mu$m). In the production of DRAM having an integration degree of 4 Gbit or more (working size is 0.15 $\mu$m or less), which requires a more precisionprecise working technology, a light source having a shorter wavelength is required and it is considered to be effective to employ photolithography using an ArF excimer laser (193 nm) and a $F_2$ excimer laser.

Particularly, ArF excimer laser lithography is considered to be as effective a precision working technology as KrF excimer laser lithography and is now studied intensively [see TAKECHI et al., Journal of Photopolymer Science and Technology, Vol. 5 (No. 3), pp. 439–446 (1992); R. D. Allen et al., Journal of Photopolymer Science and Technology, Vol. 8 (No. 4), pp. 623–636 (1995); and Vol. 9 (No. 3), pp. 465–474 (1996)].

Since the service life of a gas as a raw material of laser oscillation is short and expensive lenses are required and, furthermore, the lenses are liable to be damaged by light of laser, high sensitivity is required of a photoresist for the ArF excimer laser and $F_2$ excimer laser described above, in addition to high definition which copes with the refinement of the working size.

As the photoresist having high sensitivity, a chemically amplified resist employing a photo acid generator as a photosensitive agent is well known. The chemically amplified resist is characterized in that protonic acid generated from the photo acid generator, which is a constituent component, as a result of light irradiation causes an acid catalytic reaction to a base resin, m which is a constituent component of the resist due to a heat treatment after exposure. Thus, the chemically amplified resist has attained rapid high sensitivity as compared with a conventional resist wherein the photoreaction efficiency (reaction per photon) is 1 or less.

Typical examples of the chemically amplified resist include a photoresist made of a combination of triphenylsulfonium•hexafluoroarsetate and poly(p-tert-butoxycarbonyloxy-α-methylstyrene) described in Japanese Unexamined Patent Application, First Publication No. Hei 2-27660. It is now indispensable to develop a high sensitivity material which copes with the decrease of the wavelength of the exposure light source because almost all of photoresists to be developed are chemically amplified resists.

Examples of the photo acid generator include the triphenylsulfonium salt derivative described in Journal of the Organic Chemistry, Vol. 43, No. 15, pp. 3055–3058 (1978), the alkylsulfonium salt derivative such as cyclohexylmethyl (2-oxocyclohexyl) sulfonium trifluoromethanesulfonate disclosed in Japanese Patent Unexamined Application, First Publication No. Hei 7-28237, and the diphenyliodonium salt derivative and succinimide derivative described in Journal of the Polymer Science, Vol. 56, pp. 383–395 (1976).

In case the lithographic photoresist using a short-wavelength exposure light source, which is represented by the light of the ArF excimer laser, has low transparency, the definition is lowered and poor shape, such as trailing of the base of the pattern, is recognized. Therefore, an important technical problem of the photoresist for lithography includes, for example, improvement in transparency to exposure light.

Examples of the chemically amplified positive photoresist include those which contain at least three kinds of substances, for example, a photo acid generator, a base resin having an acid-decomposable group, and a solvent. The chemically amplified negative resist is classified into two types, that is, those which require a crosslinking agent and those which do not require a crosslinking agent. The chemically amplified negative resist, which requires the crosslinking agent, contains at least four kinds of substances, for example, a photo acid generator, a base resin capable of reacting with a crosslinking agent, a crosslinking agent, and a solvent. The chemically amplified negative resist, which does not require the crosslinking agent, contains at least three kinds of substances, for example, a photo acid generator, a base resin having a crosslinking group, and a solvent.

The photo acid generators, which are used most frequently in the ArF excimer lithography at present, are sulfonium salt compounds. Among these, a triphenylsulfonium salt derivative is used most frequently [see, for example, NOZAKI et al., Journal of Photopolymer Science and Technology, Vol. 10, No. 4, pp. 545–550 (1997); or YAMACHIKA et al., Journal of Photopolymer Science and Technology, Vol. 12, No. 4, pp. 553–560 (1999)].

However, the triphenylsulfonium salt derivative strongly absorbs far ultraviolet light having a wavelength of 220 nm or less, such as light of ArF excimer laser, because it has a benzene ring. Therefore, there was a problem that the transparency and definition of the photoresist are lowered when using the triphenylsulfonium salt derivative as the photo acid generator [see, for example, Takuya NAITO, the eighth lecture of the Society for the Study of Photoreaction and Electronic Materials, collection of abstracts of lecture, pp. 16–18 (1999)].

Therefore, β-oxocyclohexylmethyl (2-norbornyl) sulfonium triflate and cyclohexylmethyl (2-oxocyclohexyl) sulfonium triflate, which are sulfonium salt derivatives having no photobenzene ring, were developed as the photo acid generator for ArF lithography [see Proceeding of SPIE, Vol. 2195, pp. 194–204 (1994); Proceeding of SPIE, Vol. 2438, pp. 433–444 (1995)].

However, these sulfonium salt compounds have problems such as poor heat stability. The heat decomposition point of these sulfonium salt compounds is within a range of 140–150° C. in a state of a simple substance, and is lower in a resist film (resin film), e.g. 120–130° C. Accordingly, the photoresist using such a sulfonium salt compound as the photo acid generator is likely to generate an acid even at the unexposed portion as a result of decomposition when heated to 130° C. Therefore, there was a problem that the upper limit of the temperature in the heating process on formation of a resist film or the heating process after exposure is set to about 120° C.

SUMMARY OF THE INVENTION

An object of the present invention is to obtain a photo acid generator which has high transparency to far ultraviolet light, especially light of ArF excimer laser, and also has excellent heat stability.

The present inventors have studied intensively and obtained a photo acid generator (sulfonium salt compound) which has high transparency to ArF excimer laser and also has high heat decomposition point of about 200° C. Specifically, the present inventors have found that the above problems can be solved by a novel alkylsulfonium salt compound having a structure disclosed below, a photoresist composition containing the same as a constituent component, and a patterning method of patterning by light irradiation using the photoresist composition, thus completing the present invention.

The present invention provides a sulfonium salt compound represented by the following general formula (1):

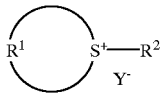

(1)

wherein $R^1$ represents a butylene group, a pentylene group, a 2-oxobutylene group, or a 2-oxopentylene group, $R^2$ represents a straight-chain, branched-chain, monocyclic, polycyclic or bridged cyclic 2-oxoalkyl group having 3 to 12 carbon atoms, or a straight-chain, branched-chain, monocyclic, polycyclic or bridged cyclic alkyl group having 3 to 12 carbon atoms, provided that either of $R^1$ and $R^2$ has an oxo group, and $Y^-$ represents a counter ion.

In one preferred embodiment of the sulfonium salt compound of the present invention, the counter ion represented by $Y^-$ in the general formula is $Z\text{-}SO_3^-$ (in which Z is $C_nF_{2n+1}$ (n is any one of 1 to 8), an alkyl group, or an alkyl-substituted or non-substituted aromatic group), $BF_4^-$, $AsF_6^-$, $SbF_6^-$, $ClO_4^-$, $Br^-$, $Cl^-$, or $I^-$.

The sulfonium salt compound of the present invention has a high heat decomposition point and is superior in heat stability and transparency to light of ArF excimer laser. Therefore, it can be preferably used as a constituent component of a photoresist composition for lithography using far ultraviolet light, especially light of ArF excimer laser as exposure light.

The present invention also provides a photo acid generator comprising a sulfonium salt compound represented by the following general formula (1):

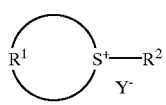

(1)

wherein $R^1$ represents an alkylene group, or an alkylene group having an oxo group, $R^2$ represents a straight-chain, branched-chain, monocyclic, polycyclic or bridged cyclic alkyl group, or a straight-chain, branched-chain, monocyclic, polycyclic or bridged cyclic alkyl group, provided that either of $R^1$ and $R^2$ has an oxo group, and $Y^-$ represents a counter ion.

In one preferred embodiment of the photo acid generator of the present invention, $R^1$ represents an alkylene group having 4 to 7 carbon atoms, or an alkylene group having an oxo group, and $R^2$ represents a straight-chain, branched-chain, monocyclic, polycyclic or bridged cyclic alkyl group having an oxo group, which has 3 to 12 carbon atoms, or a straight-chain, branched-chain, monocyclic, polycyclic or bridged cyclic alkyl group having 3 to 12 carbon atoms in the general formula (1).

In one preferred embodiment of the photo acid generator of the present invention, $R^1$ represents an alkylene group having 4 to 7 carbon atoms, or a 2-oxyalkylene group having 4 to 7 carbon atoms, and $R^2$ represents a straight-chain, branched-chain, monocyclic, polycyclic or bridged cyclic 2-oxoalkyl group having 3 to 12 carbon atoms, or a straight-chain, branched-chain, monocyclic, polycyclic or bridged cyclic alkyl group having 3 to 12 carbon atoms in the general formula (1).

In one preferred embodiment of the photo acid generator of the present invention, the counter ion represented by $Y^-$ in the general formula (1) is $Z\text{-}SO_3^-$ [in which Z is $C_nF_{2n+1}$ (n is any one of 1 to 8), an alkyl group, or an alkyl-substituted or non-substituted aromatic group], $BF_4^-$, $AsF_6^-$, $SbF_6^-$, $ClO_4^-$, $Br^-$, $Cl^-$, or $I^-$.

The photo acid generator of the present invention is superior in transparency to light of ArF excimer laser and, therefore, it can be preferably used as a constituent component of a photoresist composition for lithography using far ultraviolet light, especially light of ArF excimer laser as exposure light. Since the photo acid generator of the present invention has high heat decomposition point and excellent heat stability, the upper limit of the temperature in the heating process on formation of a resist film or the heating process after exposure is not set to about 120° C.

The present invention also provides a positive photoresist composition comprising the photo acid generator of the present invention.

The present invention also provides a negative photoresist composition comprising the photo acid generator of the present invention.

The photoresist composition of the present invention is suited for lithography using exposure light having a short wavelength, such as ArF excimer laser lithography, because of its high sensitivity and excellent definition.

Furthermore, the present invention provides a pattern forming method, which comprises forming a thin film on a substrate using the photoresist composition of the present invention, exposing to light having a wavelength of 300 nm or less, and developing to form a pattern.

In one preferred embodiment of the pattern forming method of the present invention, the exposure light is light of ArF excimer laser.

In one preferred embodiment of the pattern forming method of the present invention, the exposure light is light of $F_2$ excimer laser.

Use of the pattern forming method of the present invention makes it possible to form a precision pattern required to produce a semiconductor device.

DESCRIPTION OF THE PREFERRED EMBODIMENTS

Figure 1:
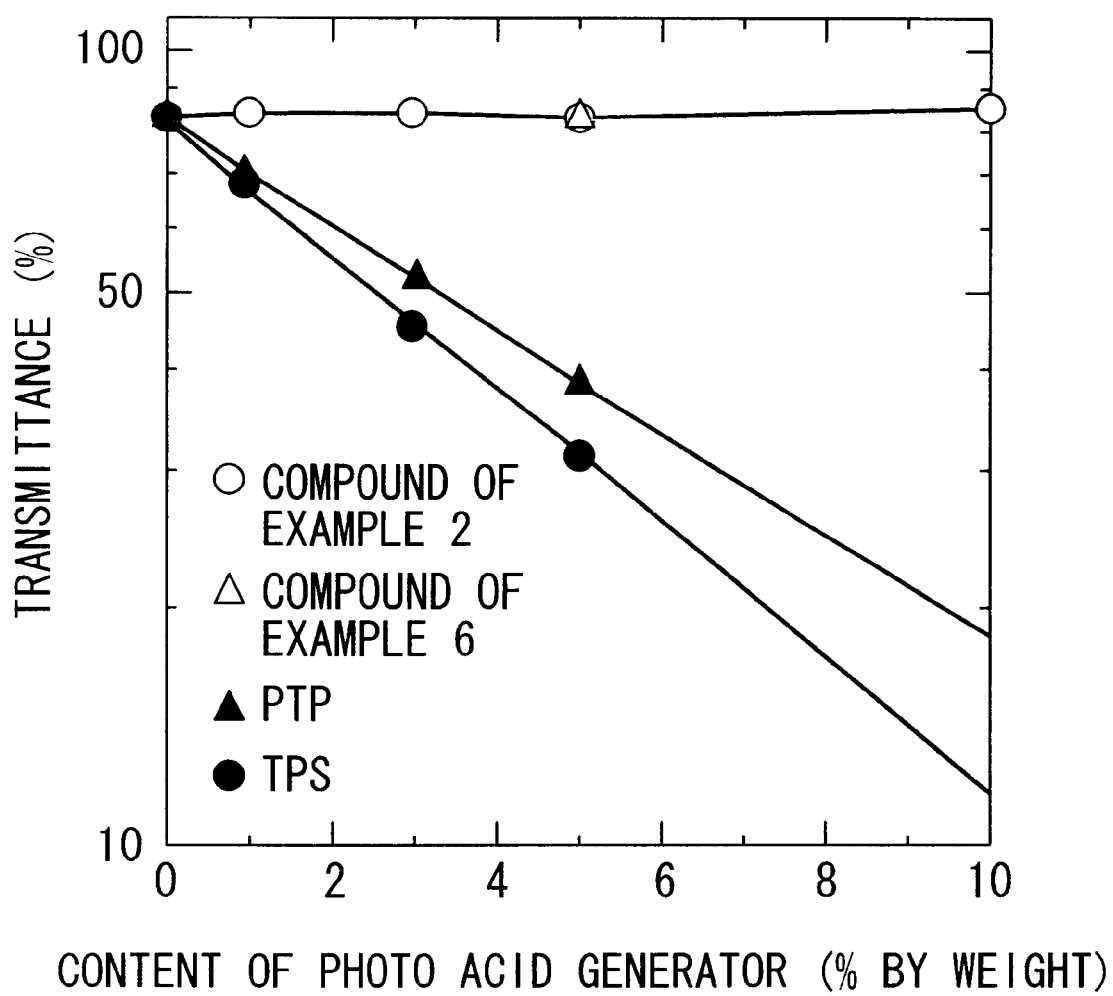
FIG. 1 is a graph showing the results of the transmittance in Experiment 6.

The sulfonium salt compound of the present invention is represented by the general formula (1).

In the general formula (1), $R^1$ represents an alkylene group, or an alkylene group having an oxo group, preferably an alkylene group having 4 to 7 carbon atoms, or an alkylene group having an oxo group, and more preferably an alkylene group having 4 to 7 carbon atoms, or a 2-oxoalkylene group having 4 to 7 carbon atoms. Specific examples thereof include propylene group, butylene group, pentylene group, hexylene group, heptylene group, 1-oxopropylene group, 2-oxopropylene group, 1-oxobutylene group, 2-oxobutylene group, 1-oxopentylene group, 2-oxopentylene group, 3-oxopentylene group, 1-oxohexylene group, 2-oxohexylene group, 3-oxohexylene group, 1-oxoheptylene group, 2-oxoheptylene oxoheptylene group, 3-oxoheptylene group, and 4-oxoheptylene group. Among these groups, butylene group, pentylene group, 2-oxobutylene group and 2-oxopentylene group are preferable.

In the general formula (1), $R^2$ represents a straight-chain, branched-chain, monocyclic, or bridged cyclic alkyl group having an oxo group, or a straight-chain, branched, monocyclic or bridged cyclic alkyl group, and preferably a straight-chain, branched-chain, monocyclic, polycyclic or bridged cyclic alkyl group having an oxo group, which has 3 to 12 carbon atoms, or a straight-chain, branched-chain, monocyclic, polycyclic or bridged cyclic alkyl group having 3 to 12 carbon atoms.

Specific examples of the straight-chain, branched-chain, monocyclic, polycyclic or bridged cyclic alkyl group having an oxo group, which has 3 to 12 carbon atoms, include 2-oxo-propyl group, 2-oxo-butyl group, 2-oxo-3-methyl-butyl group, 2-oxo-3,3-dimethyl-butyl group, 2-oxo-pentyl group, 2-oxo-3-methyl-pentyl group, 2-oxo-3,3-dimethyl-pentyl group, 2-oxo-4-ethyl-pentyl group, 2-oxo-4,4-diethyl-pentyl group, 2-oxo-3-ethyl-pentyl group, 2-oxo-3,3-diethyl-pentyl group, 2-oxo-4-methyl-4-ethyl-pentyl group, 2-oxo-hexyl group, 2-oxo-3-methyl-hexyl group, 2-oxo-3,3-dimethyl-hexyl group, 2-oxo-4,4-dimethyl-hexyl group, 2-oxo-5,5-dimethyl-hexyl group, 2-oxo-3-ethyl-hexyl group, 2-oxo-4-ethyl-hexyl group, 2-oxo-heptyl group, 2-oxo-3-methyl-heptyl group, 2-oxo-4-methyl-heptyl group, 2-oxo-5-methyl-heptyl group, 2-oxo-6-methyl-heptyl group, 2-oxo-6,6-dimethyl-heptyl group, 2-oxo-3-ethyl-heptyl group, 2-oxo-4-ethyl-heptyl group, 2-oxo-5-ethyl-heptyl group, 2-oxo-3-propyl-heptyl group, 2-oxo-4-propyl-heptyl group, 2-oxo-octyl group, 2-oxo-3-methyl-octyl group, 2-oxo-4-methyl-octyl group, 2-oxo-5-methyl-octyl group, 2-oxo-6-methyl-octyl group, 2-oxo-7-methyl-octyl group, 2-oxo-7,7-dimethyl-octyl group, 2-oxo-3-ethyl-octyl group, 2-oxo-4-ethyl-octyl group, 2-oxo-5-ethyl-octyl group, 2-oxo-cyclopentyl group, 2-oxo-cyclohexyl group, 2-oxo-cycloheptyl group, 2-oxo-cyclopropylmethyl group, 2-oxo-methylcyclohexyl group, 2-oxo-cyclohexylmethyl group, 2-oxo-norbornyl group, 2-oxo-tricyclodecyl group (especially 2-oxo-tricyclo $[5.2.1.0^{2,6}]$ decyl group), 2-oxo-tetracyclodecyl group (especially 2-octylcyclohexyl group, oxo-tetracyclo $[4.4.0^{2,5}.1^{7,10}]$ decyl group), 2-oxo-bornyl group, 2-oxo-2-cyclohexyl-ethyl group, and 2-oxo-2-cyclopentyl-ethyl group.

Specific examples of the straight-chain, branched-chain, monocyclic, polycyclic or bridged cyclic alkyl group having 3 to 12 carbon atoms include propyl group, butyl group, 2-methyl-butyl group, 3-methyl-butyl group, 3,3-dimethyl-butyl group, pentyl group, 2-methyl-pentyl group, 3-methyl-pentyl group, 4-methyl-pentyl group, 4,4-dimethyl-pentyl group, 2-ethyl pentyl group, 3-ethyl pentyl group, hexyl group, 3-methyl-hexyl group, 4-methyl-hexyl group, 5-methyl-hexyl group, 5,5-dimethyl-hexyl group, 2-ethyl-hexyl group, 3-ethyl-hexyl group, 4-ethyl-hexyl group, heptyl group, 2-methyl-heptyl group, 3-methyl-heptyl group, 4-methyl-heptyl group, 5-methyl-heptyl group, 6-methyl-heptyl group, 6,6-dimethyl-heptyl group, 2-ethyl-heptyl group, 3-ethyl-heptyl group, 4-ethyl-heptyl group, 5-ethyl-heptyl group, octyl group, 2-methyl-octyl group, 3-methyl-octyl group, 4-methyl-octyl group, 5-methyl-octyl group, 6-methyl-octyl group, 7-methyl-octyl group, 7,7-dimethyl-octyl group, 2-ethyl-octyl group, 2-ethyl-octyl group, 3-ethyl-octyl group, 4-ethyl-octyl group, 5-ethyl-octyl group, cyclopentyl group, cyclohexyl group, cycloheptyl group, cyclopropylmethyl group, methylcyclohexyl group, cyclohexylmethyl group, norbornyl group, tricyclodecyl group (especially tricyclo $[5.2.1.0^{2,6}]$ decyl group), adamantyl group, bornyl group, and tetracyclodecyl group (especially tetracyclo $[4.4.0^{2,6}.1^{7,10}]$ decyl group).

In the general formula (1), at least one of groups represented by $R^1$ and $R^2$ must have an oxo group.

In the general formula (1), $Y^-$ represents a counter ion and specific examples thereof include sulfonate ion having a fluorocarbon group, such as $BF_4^-$ (tetrafluoroborate ion), $AsF_6^-$ (hexafluoroarsenate ion), $SbF_6^-$ (hexafluoroantimonate ion), $PF_6^-$ (hexafluorophosphate ion), $CF_3SO_3^-$ (trifluoromethanesulfonate ion), $C_2F_5SO_3^-$ (pentafluoroethanesulfonate ion), $C_3F_7SO_3^-$ (heptafluoropropanesulfonate ion), $C_4F_9SO_3^-$ (nonafluorobutanesulfonate ion), $C_5F_{11}SO_3^-$ (dodecafluoropentanesulfonate ion), $C_6F_{13}SO_3^-$ (tridecafluorohexanesulfonate ion), $C_7F_{15}SO_3^-$ (pentadecafluoroheptanesulfonate ion), or $C_8F_{17}SO_3^-$ (heptadecafluorooctanesulfonate ion); alkylsulfonate ion such as $CH_3SO_3^-$ (methanesulfonate ion), $C_2H_5SO_3^-$ (ethanesulfonate ion), $C_3H_7SO_3^-$ (propanesulfonate ion), $C_4H_9SO_3^-$ (butanesulfonate ion), $C_5H_{11}SO_3^-$ (pentanesulfonate ion), $C_6H_{13}SO_3^-$ (hexanesulfonate ion), $C_7H_{15}SO_3^-$ (heptanesulfonate ion), $C_8H_{17}SO_3^-$ (octanesulfonate ion), cyclohexanesulfonate ion, or camphorsulfonate ion; sulfonate ion having an aromatic group, such as benzenesulfonate ion, toluenesulfonate ion, naphthalenesulfonate ion, anthracenesulfonate ion, fluorobenzenesulfonate ion, difluorobenzenesulfonate ion, trifluorobenzenesulfonate ion, chlorobenzenesulfonate ion, dichlorobenzenesulfonate ion, or trichlorobenzenesulfonate ion; $ClO_4^-$ (perchlorate ion), Br (bromine ion), Cl⁻ (chlorine ion), or I⁻ (iodine ion). Among these ions, $Z-SO_3^-$ [Z is $C_nF_{2n+1}$ (n is any one of 1 to 8), an alkyl group, or an alkyl-substituted or non-substituted aromatic group), $BF_4^-$, $AsF_6^-$, $SbF_6^-$, $ClO_4^-$, Br⁻, Cl⁻, or I⁻] are preferable.

One example of the method of synthesizing the sulfonium salt compound represented by the general formula (1) will be described below.

A cyclic sulfide compound represented by the following general formula (2) is dissolved in acetone and a halogenated alkyl represented by the general formula (3) is added to the solution. After the mixture was reacted for 0.5 to 24 hours, the deposit is collected by filtration. The deposit is washed with an insoluble solvent such as diethyl ether and dried to obtain a sulfonium salt compound represented by the general formula (4) wherein $Y^-$ in the general formula (1) is a halogen ion. The resulting sulfonium salt compound represented by the general formula (4) is dissolved in acetonitrile and an organometallic salt represented by the general formula (5) is added. Then, a large amount of chloroform is added to deposit a halogenated metal, which is removed by filtration. The solvent contained in the resulting filtrate is distilled off under reduced pressure and the residue is recrystallized from a proper solvent (e.g. ethyl acetate, etc.), thereby making it possible to obtain a sulfonium salt compound represented by the general formula (1).

(2)

wherein $R^1$ represents an alkylene group, or an alkylene group having an oxo group.

(3)

wherein $R^2$ represents a straight-chain, branched-chain, monocyclic, polycyclic or bridged cyclic alkyl group having an oxo group, or a straight-chain, branched-chain, monocyclic, polycyclic or bridged cyclic alkyl group, and X represents a halogen atom such as iodine, bromine, or chlorine.

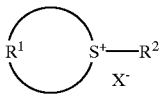
(4)

wherein $R^1$ represents an alkylene group, or an alkylene group having an oxo group, $R^2$ represents a straight-chain, branched-chain, monocyclic, polycyclic or bridged cyclic alkyl group having an oxo group, or a straight-chain, branched-chain, monocyclic, polycyclic or bridged cyclic alkyl group, and X represents a halogen atom such as iodine, bromine, or chlorine.

(5)

wherein $Y^-$ represents $Z\text{-}SO_3^-$ (in which Z is $C_nF_{2n+1}$ (n is any one of 1 to 8), an alkyl group, or an alkyl-substituted or non-substituted aromatic group), $BF_4^-$, $AsF_6^-$, $SbF_6^-$, $ClO_4^-$, $Br^-$, $Cl^-$, or $I^-$, and W represents an atom of metal such as potassium, sodium or silver.

The sulfonium salt compound represented by the general formula (1) thus obtained is suited for use as a constituent component of a resist for ArF excimer laser lithography because of its remarkably less light absorption within a far ultraviolet range of light of ArF excimer laser and excellent transparency to exposure light. The sulfonium salt compound is particularly superior in transparency to photo acid generators having an aromatic ring, such as triphenylsulfonium salt and phenancylthiacyclohexanium salt. The sulfonium salt compound causes less light absorption to light of not only ArF excimer laser, but also KrF excimer laser and $F_2$ excimer laser and has excellent transparency and, therefore, it can be used as a photo acid generator for resist using the above light as exposure light.

The heat decomposition point of the sulfonium salt is higher than that of a conventional photo acid generator for ArF lithography, such as β-oxocyclohexylmethyl(2-norbornyl) sulfonium triflate or cyclhexylmethyl(2-oxocyclohexyl) sulfonium triflate, and is superior in heat stability.

The positive photoresist composition and negative photoresist composition serving as the photoresist composition of the present invention can be obtained by using the sulfonium salt compound represented by the general formula (1) as the photo acid generator.

The positive photoresist composition can be obtained by blending a photo acid generator, a positive base resin having an acid-decomposable group and a solvent as an essential component.

The negative photoresist composition can be obtained by blending a photo acid generator, a negative base resin capable of reacting with a crosslinking agent, a crosslinking agent and a solvent as an essential component, or blending a photo acid generator, a negative base resin having a crosslinking group and a solvent as an essential component.

The sulfonium salt compound represented by the general formula (1) used as the photo acid generator in the photoresist composition of the present invention is used alone, or two or more of them are used in combination.

The photo acid generator is blended in the amount within a range from 0.1 to 40 parts by weight, and preferably from 1 to 25 parts by weight, based on 100 parts by weight of the whole solid component (including the photo acid generator) of the photoresist composition of the present invention. When the amount is 0.1 parts by weight or less, the sensitivity tends to be drastically lowered, thus making it difficult to form a pattern. On the other hand, when the amount exceeds 40 parts by weight, it tends to become difficult to form a uniform coated film and the residue (scum) is liable to occur after the development.

As the positive base resin used in the positive photoresist composition of the present invention, for example, a resin, which has high transparency to wavelength of exposure light, especially exposure light of an ArF excimer laser, and is made soluble in an alkali developer as a result of an action of an acid, is appropriately used. Specifically, resins represented by the following general formulas (6) to (9) are preferably used.

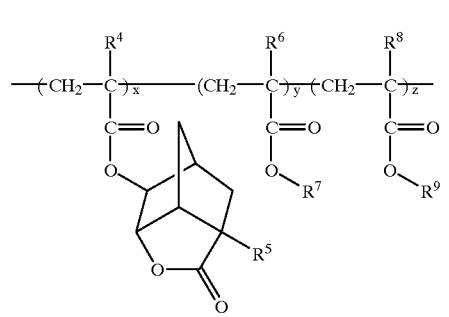
(6)

Wherein $R^4$, $R^5$, $R^6$ and $R^8$ represent a hydrogen atom or a methyl group, $R^7$ represents a group capable of being decomposed by an acid, or a carboxylated bridged cyclic hydrocarbon group having 7 to 13 carbon atoms, which is protected with a group capable of being decomposed by an acid, $R^9$ represents a hydrogen atom, a hydrocarbon group having 7 to 13 carbon atoms, or a cyclic hydrocarbon group having a carboxyl group, which has 7 to 13 carbon atoms, x, y and z represent an arbitrary numeral which satisfies the following expressions: x+Y+Z=1, 0<x<1, 0<y<1 and 0≦z<1, and a weight-average molecular weight of a polymer is within a range from 2,000 to 200,000.

(7)

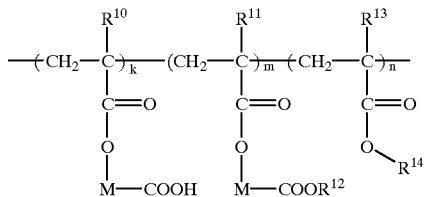

Wherein $R^{10}$, $R^{11}$ and $R^{13}$ represent a hydrogen atom or a methyl group, M represents a group having a bridged cyclic hydrocarbon group, which has 7 to 13 carbon atoms, $R^{12}$ represents a group capable of being decomposed by an acid, $R^{14}$ represents a hydrogen atom or a hydrocarbon group having 1 to 12 carbon atoms, k, m and n represent an arbitrary numeral which satisfies the following expressions: k+m+n=1, 0<k<1, 0<m <1 and 0≦n<1, and a weight-average molecular weight of a polymer is within a range from 2,000 to 200,000.

(8)

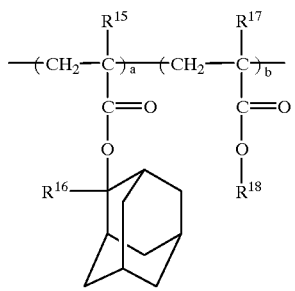

Wherein $R^{15}$, $R^{16}$ and $R^{17}$ represent a hydrogen atom or a methyl group, $R^{18}$ represents a group having a lactone structure, a and b represent an arbitrary numeral which satisfies the following expressions: a+b=1, 0<a<1 and 0<b<1, and a weight-average molecular weight of a polymer is within a range from 2,000 to 200,000.

(9)

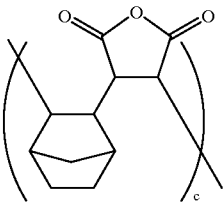

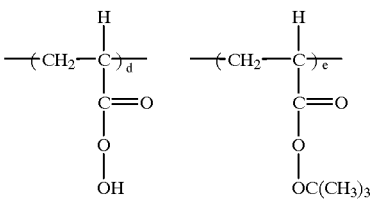

Wherein c, d and e represent an arbitrary numeral which satisfies the following expressions: c+d+e=1, 0≦c<1, 0<d<1 and 0<e<1, and a weight-average molecular weight of a polymer is within a range from 2,000 to 200,000.

The positive base resin is usually blended in the amount within a range from 60 to 98.8 parts by weight, and preferably from 75 to 99 parts by weight, based on 100 parts by weight of the total constituent components of the positive photoresist composition, excluding the solvent component. When the amount is 60 parts by weight or less, it tends to become difficult to form a uniform coated film. On the other hand, when the amount exceeds 99.8 parts by weight, the sensitivity tends to be drastically lowered.

As the negative base resin used in the negative photoresist composition of the present invention, for example, a resin, which has high transparency to exposure light such as light of ArF excimer laser, and is capable of reacting with a crosslinking agent or has a crosslinking group, is appropriately used. Specifically, resins represented by the following general formulas (10) to (11) are preferably used.

(10)

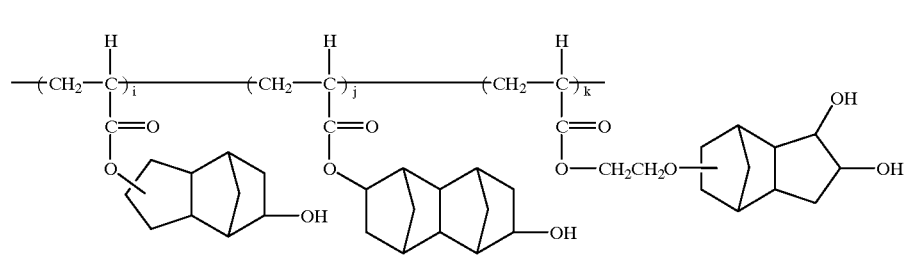

Wherein i, j and k represent an arbitrary numeral which satisfies the following expressions: i+j+k=1, 0≦i<1, 0<j<1 and 0≦k<1, and a weight-average molecular weight of a polymer is within a range from 2,000 to 200,000.

(11)

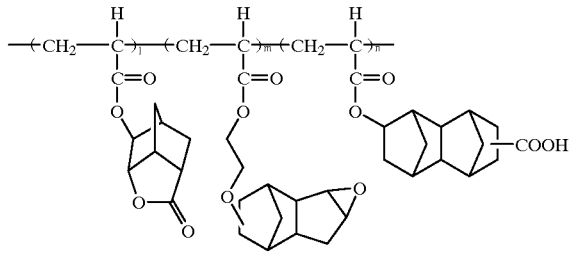

Wherein l, m and n represent an arbitrary numeral which satisfies the following expressions: l+m+n=1, 0≦l<1, 0<m<1 and 0<n<1, and a weight-average molecular weight of a polymer is within a range from 2,000 to 200,000.

The negative base resin is usually blended in the amount within a range from 60 to 98.8 parts by weight, and preferably from 75 to 99 parts by weight, based on 100 parts by weight of the total constituent components of the negative photoresist composition, excluding the solvent component. When the amount is 60 parts by weight or less, it tends to become difficult to form a uniform coated film. On the other hand, when the amount exceeds 99.8 parts by weight, the sensitivity tends to be drastically lowered.

A crosslinking agent capable of crosslinking a resin in the exposed portion thereby to insolubilize the resin can be added to the negative photoresist composition. The crosslinking agent is not be specifically limited, but there can be preferably used urea • melamine crosslinking agents such as hexamethoxymethylmelamine, 1,3,4,6-tetrakis (methoxymethyl) glycol uril, 1,3-bis(methoxymethyl)-4,5-bis (methoxymethyl) ethylene urea, and 1,3-bis (methoxymethyl)urea, and polyfunctional compounds. The crosslinking agent may be added alone, or two or more of them may be used in combination.

As the crosslinking accelerator, for example, polyhydric alcohols having an effect of improving the crosslink density may be added furthermore. Specific examples of the crosslinking accelerator include 2,3-dihydroxy-5-hydroxymethylnorbornene, 1,4-cyclohexanedimethanol, and 3,4,8(9)-trihydroxytricyclodecane.

As the solvent, which can be used in the photoresist composition of the present invention, any solvent can be used as far as it can sufficiently dissolve the photo acid generator and base resin, and can form a uniform coated film from the solution by means of a spin coating method. Specific examples of the solvent include n-propyl alcohol, isopropyl alcohol, n-butyl alcohol, tert-butyl alcohol, methylcellosolve acetate, ethylcellosolve acetate, propylene glycol monoethyl acetate, methyl lactate, ethyl lactate, 2-methoxybutyl acetate, 2-methoxyethyl acetate, methyl pyruvate, ethyl pyruvate, methyl 3-methoxypropionate, ethyl 3-methoxypropionate, N-methyl-2-pyrrolidione, cyclohexanone, cyclopentanone, cyclohexanol, methyl ethyl ketone, 1,4-dioxane, ethylene glycol monomethyl ether, ethylene glycol monomethyl ether acetate, ethylene glycol monoethyl ether, ethylene glycol monoisopropyl ether, diethylene glycol monomethyl ether, and diethylene glycol dimethyl ether. The solvent can be used alone, or a mixture of two or more of them can be used.

The amount of the solvent is usually blended in the amount within a range from 70 to 90 parts by weight, and preferably from 80 to 88 parts by weight, based on 100 parts by weight of the total constituent components of the photoresist composition of the present invention.

If necessary, surfactants, pigments, stabilizers, applicability modifiers and dyes can be appropriately added to the photoresist composition of the present invention, in addition to the above essential constituent components.

A pattern can be formed by coating the resulting photoresist composition of the present invention on a substrate made of silicon by means of a known film forming method such as spin coating method to form a uniform coated film, exposing to light having a wavelength of 300 nm or less, such as light of ArF excimer laser or $F_2$ excimer laser, and developing by means of a known developing method to form a pattern.

Regarding the developer used in the development process, for example, proper organic solvents or mixed solvents thereof, or aqueous alkali solutions having a proper concentration or mixtures with organic solvents may be selected according to the solubility of the photoresist composition to be used. Examples of the organic solvent include acetone, methyl ethyl ketone, methyl alcohol, ethyl alcohol, isopropyl alcohol, tetrahydrofuran, and dioxane. Examples of the alkali solution include, but are not limited to, solutions and aqueous solution which contain inorganic alkalis such as sodium hydroxide, potassium hydroxide, sodium silicate, and ammonia; organic amines such as ethylamine, propylamine, diethylamine, dipropylamine, trimethylamine, and triethylamine; and organic ammonium salts such as tetramethylammonium hydroxide, tetraethylammonium hydroxide, trimethylhydroxymethylammonium hydroxide, triethylhydroxymethylammonium hydroxide, and trimethylhydroxyethylammonium hydroxide.

If necessary, other components such as surfactants can be added appropriately to the developer.

EXAMPLES

The following Examples and Experiments further illustrate the present invention in detail, but the present invention is not limited by these Examples.

Example 1

2-oxobutyl-thiacyclohexanium bromide represented by the following formula was synthesized.

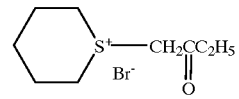

The following synthesis operation was carried out under a yellow lamp.

In a 100 ml three-necked flask, 4 g of pentamethylene sulfide was dissolved in 40 ml of acetone. To the solution, 6 g of 1-bromo-2-butanone was added dropwise while stirring. After leaving for 24 hours, the deposited white crystal was collected by filtration. The white crystal was ground to a powder, which was washed with ether. The powder was dried by a vacuum drier at 30° C. for six hours to obtain 7.2 g of 2-oxobutyl-thiacyclohexanium bromide (yield: 72.5%).

The NMR analysis results of the resulting synthesized material are as follows. AMX400 manufactured by Bulker Co. was used as NMR.

$^1$H-NMR (CDCl$_3$, internal standard: tetramethylsilane): δ (ppm) 1.11–1.18 (t, 3H, —CH$_3$), 1.85–1.91 (m, 4H, —CH$_2$—), 2.27–2.39 (m, 2H, —CH$_2$—), 2.67–2.81 (m, 2H, —CH$_2$—), 3.73–3.86 (m, 2H, S$^+$—CH$_2$—), 4.09–4.12 (m, 2H, S$^+$—CH$_2$—), 5.77 (s, 2H, S$^+$—CH$_2$—C(O)—).

The elemental analysis results are as follows (the following theoretical value shows a calculated value to C$_9$H$_{17}$BrOS (MW253.19)).

Elemental Analysis

|  | C | H | S |
|---|---|---|---|
| Found value (% by weight) | 42.69 | 6.77 | 12.66 |
| Theoretical value (% by weight) | 42.50 | 6.85 | 12.53 |

Example 2

2-oxobutyl-thiacyclohexanium trifluoromethanesulfonate represented by the following formula was synthesized.

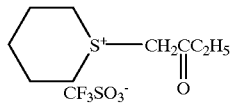

The following synthesis operation was carried out under a yellow lamp.

In a 300 ml three-necked flask, 2 g of 2-oxobutyl-thiacyclohexanium bromide obtained in Example 1 was dissolved in 10 ml of acetonitrile. To the solution, a solution prepared by dissolving 1.5 g of a potassium trifluoromethanesulfonate salt in 100 ml of acetonitrile was added dropwise. After stirring for three hours, the deposited potassium bromide was removed by filtration and acetonitrile was distilled off under reduced pressure by an evaporator. The residue was dissolved in chloroform and the insoluble matter was removed by filtration. Chloroform in the filtrate was distilled off under reduced pressure and the residue (transparent viscous liquid) was cooled in a refrigerator at −20° C. for three hours. The residue was converted into a white crystal by cooling. The white crystal was recrystallized from ethyl acetate and then dried under reduced pressure at 30° C. for six hours to obtain 1.92 g of 2-oxobutyl-thiacyclohexanium trifluoromethanesulfonate (yield: 75.4%).

The NMR analysis results of the resulting synthesized material are as follows. $^1$H-NMR (CDCl$_3$, internal standard: tetramethylsilane): δ (ppm) 1.04–1.11 (t, 3H, —CH$_3$), 1.82–1.92 (m, 4H, —CH$_2$—), 2.14–2.26 (m, 2H, —CH$_2$—), 2.65–2.70 (m, 2H, —CH$_2$—), 3.42–3.46 (m, 2H, S$^+$—CH$_2$—), 3.42–3.46 (m, 2H, S$^+$—CH$_2$—), 3.56–3.59 (m, 2H, S$^+$—CH$_2$—), 4.89 (s, 2H, S$^+$—CH$_2$—C(O)—)

The elemental analysis results are as follows (the following theoretical value shows a calculated value to C$_{10}$H$_{17}$F$_3$O$_4$S$_2$ (MW322.35)).

Elemental Analysis

|  | C | H | S |
|---|---|---|---|
| Found value (% by weight) | 47.26 | 5.32 | 19.89 |
| Theoretical value (% by weight) | 47.26 | 5.40 | 19.99 |

The melting point was 51.4° C. and the heat decomposition point was 212.8° C.

Example 3

2-oxobutyl-thiacyclohexanium nonafluorobutanesulfonate represented by the following formula was synthesized.

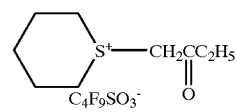

The following synthesis operation was carried out under a yellow lamp.

In the same manner as in Example 2, except that 2.72 g of a potassium nonafluorobutanesulfonate salt was used in place of 1.5 g of the potassium trifluoromethanesulfonate salt, the synthesis test of 2-oxobutyl-thiacyclohexanium nonafluorobutanesulfonate was conducted. As a result, 1.42 g of 2-oxobutyl-thiacyclohexanium nonafluorobutanesulfonate was obtained (yield: 38%).

The NMR analysis results of the resulting synthesized material are as follows. $^1$H-NMR (CDCl$_3$, internal standard: tetramethylsilane): δ (ppm) 1.06–1.12 (t, 3H, —CH$_3$), 1.82–1.95 (m, 4H, —CH$_2$—), 2.27–2.35 (m, 2H, —CH$_2$—), 2.66–2.71 (m, 2H, —CH$_2$—), 3.45–3.46 (m, 2H, S$^+$—CH$_2$—), 3.40–3.65 (m, 4H, S$^{+-CH}{}_2$—), 4.93 (s, 2H, S$^+$—CH$_2$—C(O)—).

The elemental analysis results are as follows [the following theoretical value shows a calculated value to C$_{13}$H$_{17}$F$_9$O$_4$S$_2$ (MW472.38)].

Elemental Analysis

|  | C | H | S |
|---|---|---|---|
| Found value (% by weight) | 33.05 | 3.63 | 13.57 |
| Theoretical value (% by weight) | 33.23 | 3.74 | 13.62 |

The melting point was 37.7° C. and the heat decomposition point was 238.4° C.

Example 4

2-oxobutyl-thiacyclohexaniumheptadecafluorooctasulfonate represented by the following formula was synthesized.

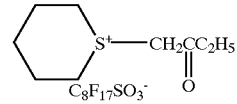

The following synthesis operation was carried out under a yellow lamp.

In the same manner as in Example 2, except that 5.38 g of a potassium heptadecafluorooctasulfonate salt was used in place of 1.5 g of the potassium trifluoromethanesulfonate salt, the synthesis test of 2-oxobutyl-thiacyclohexanium heptadecafluorooctasulfonate was conducted. As a result, 1.54 g of 2-oxobutyl-thiacyclohexanium heptadecafluorooctasulfonate was obtained (yield: 58%).

The NMR analysis results of the resulting synthesized material are as follows. $^1$H-NMR (CDCl$_3$, internal standard: tetramethylsilane): δ (ppm) 1.05–1.11 (t, 3H, —CH$_3$), 1.82–1.92 (m, 4H, —CH$_2$—), 2.24–2.28 (m, 2H, —CH$_2$—), 2.66–2.71 (m, 2H, —CH$_2$—), 3.48–3.46 (m, 2H, S$^+$—CH$_2$—), 3.42–3.62 (m, 4H, S$^+$13 CH$_2$—), 4.99 (s, 2H, S$^+$—CH$_2$—C(O)—).

The elemental analysis results are as follows [the following theoretical value shows a calculated value to C$_{17}$H$_{17}$F$_{17}$O$_4$S$_2$ (MW672.41)].

Elemental Analysis

|  | C | H | S |
|---|---|---|---|
| Found value (% by weight) | 30.37 | 2.55 | 9.54 |
| Theoretical value (% by weight) | 30.65 | 2.41 | 9.88 |

Example 5

2-oxobutyl-thiacyclopentamium bromide represented by the following formula was synthesized.

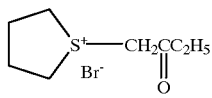

The following synthesis operation was carried out under a yellow lamp.

In a 100 ml three-necked flask, 3.5 g of tetrahydrothiophene was dissolved in 40 ml of acetone. To the solution, 6 g of 1-bromo-2-butanone was added dropwise while stirring. After leaving for 24 hours, the deposited white crystal was collected by filtration. The white crystal was ground to a powder, which was washed with ether. The powder was dried by a vacuum drier at 30° C. for six hours to obtain 6.86 g of 2-oxobutyl-thiacyclopentanium bromide (yield: 72.2%).

The NMR analysis results of the resulting synthesized material are as follows. $^1$H-NMR (CDCl$_3$, internal standard: tetramethylsilane): δ (ppm) 1.05–1.18 (t, 3H, —CH$_3$), 2.36–2.40 (m, 2H, —CH$_2$—), 2.56–2.62 (m, 2H, —CH$_2$—), 2.74–2.81 (m, 2H, —CH$_2$—), 3.75–3.86 (m, 4H, S$^+$—CH$_2$—), 5.5 (s, 2H, S$^+$—CH$_2$—C(O)—)

The elemental analysis results are as follows (the following theoretical value shows a calculated value to C$_9$H$_{15}$BrOS (MW239.17)).

Elemental Analysis

|  | C | H | S |
|---|---|---|---|
| Found value (% by weight) | 40.14 | 6.32 | 13.40 |
| Theoretical value (% by weight) | 40.25 | 6.55 | 13.14 |

Example 6

2-oxobutyl-thiacyclopentanium trifluoromethanesulfonate represented by the following formula was synthesized.

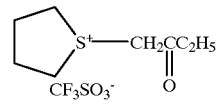

The following synthesis operation was carried out under a yellow lamp.

In a 300 ml three-necked flask, 2 g of 2-oxobutyl-thiacyclohexanium bromide obtained in Example 1 was dissolved in 10 ml of acetonitrile. To the solution, a solution prepared by dissolving 1.6 g of a potassium trifluoromethanesulfonate salt in 100 ml of acetonitrile was added dropwise. After stirring for three hours, the deposited potassium bromide was removed by filtration and acetonitrile was distilled off under reduced pressure by an evaporator. The residue was dissolved in chloroform and the insoluble matter was removed by filtration. Chloroform in the filtrate was distilled off under reduced pressure and the residue (transparent viscous liquid) was cooled in a refrigerator at –20° C. for three hours. The residue was converted into a white crystal by cooling. The white crystal was recrystallized from ethyl acetate and then dried under reduced pressure at 30 ° C. for six hours to obtain 1.7 g of 2-oxobutyl-thiacyclopentanium trifluoromethanesulfonate (yield: 65.8%).

The NMR analysis results of the resulting synthesized material are as follows. $^1$H-NMR (CDCl$_3$, internal standard: tetramethylsilane): δ (ppm) 1.04–1.13 (t, 3H, —CH$_3$), 2.28–2.31 (m, 2H, —CH$_2$—), 2.46–2.49 (m, 2H, —CH$_2$—), 2.63–2.71 (m, 2H, —CH$_2$—), 3.49–3.68 (m, 4H, S$^+$—CH$_2$—), 4.82 (s, 2H, S$^+$—CH$_2$—C(O)—).

The elemental analysis results are as follows (the following theoretical value shows a calculated value to C$_9$H$_{15}$F$_3$O$_4$S$_2$ (MW308.33)).

Elemental Analysis

|  | C | H | S |
|---|---|---|---|
| Found value (% by weight) | 35.0 | 4.90 | 20.80 |
| Theoretical value (% by weight) | 35.12 | 4.78 | 20.59 |

The melting point was 59.6° C. and the heat decomposition point was 225.7° C.

Example 7

2-oxobutyl-thiacyclopentanium nonafluorobutanesulfonate represented by the following formula was synthesized.

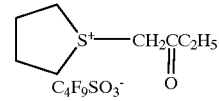

The following synthesis operation was carried out under a yellow lamp.

In the same manner as in Example 2, except that 2.88 g of a potassium nonafluorobutanesulfonate salt was used in place of 1.6 g of the potassium trifluoromethanesulfonate salt, the synthesis test of 2-oxobutyl-thiacyclopentanium nonafluorobutanesulfonate was conducted. As a result, 2.54 g of 2-oxobutyl-thiacyclopentanium nonafluorobutanesulfonate was obtained (yield: 38%).

The NMR analysis results of the resulting synthesized material are as follows. $^1$H-NMR (CDCl$_3$, internal standard: tetramethylsilane): δ (ppm) 1.05–1.07 (t, 3H, —CH$_3$), 2.28–2.32 (m, 4H, —CH$_2$—), 2.43–2.47 (m, 2H, —CH$_2$—), 2.63–2.69 (m, 2H, —CH$_2$—), 3.48–3.52 (m, 2H, S$^+$—CH$_2$—), 3.65–3.68 (m, 2H, S$^{+-CH}{}_2$—), 4.78 (s, 2H, S$^+$—CH$_2$—C(O)—).

The elemental analysis results are as follows (the following theoretical value shows a calculated value to C$_{12}$H$_{15}$F$_9$O$_4$S$_2$ (MW458.35)).

Elemental Analysis

|  | C | H | S |
|---|---|---|---|
| Found value (% by weight) | 31.45 | 3.30 | 13.99 |
| Theoretical value (% by weight) | 31.56 | 3.33 | 13.95 |

The melting point was 61.3° C. and the heat decomposition point was 236.4° C.

Example 8

2-oxo-3,3-dimethylbutyl-thiacyclopentanium bromide represented by the following formula was synthesized.

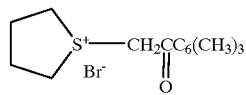

The following synthesis operation was carried out under a yellow lamp.

In a 300 ml three-necked flask, 2 g of tetrahydroxythiophene was dissolved in 20 ml of acetone. To the solution, 4.87 g of 1-bromo-3,3-dimethy 2-butanone was added dropwise while stirring. After leaving for 24 hours, the deposited white crystal was collected by filtration. The white crystal was ground to a powder, which was washed with ether. The powder was dried by a vacuum drier at 30° C. for six hours to obtain 5.15 g of 2-oxo-3,3-dimethylbutyl-thiacyclopentanium bromide (yield: 75.0%).

The NMR analysis results of the resulting synthesized material are as follows. $^1$H-NMR (CDCl$_3$, internal standard: tetramethylsilane): δ (ppm) 1.28–1.33 (t, 9H, —CH$_3$), 2.34–2.41 (m, 2H, —CH$_2$—), 2.56–2.63 (m, 2H, —CH$_2$—), 2.74–2.81 (m, 2H, —CH$_2$—), 3.77–3.88 (m, 4H, S$^+$—CH$_2$—), 5.5 (s, 2H, S$^+$—CH$_2$—C(O)—).

The elemental analysis results are as follows (the following theoretical value shows a calculated value to C$_{10}$H$_{19}$BrOS (MW267.22)).

Elemental Analysis

|  | C | H | S |
|---|---|---|---|
| Found value (% by weight) | 45.08 | 7.10 | 11.95 |
| Theoretical value (% by weight) | 44.95 | 7.17 | 12.00 |

Example 9

2-oxo-3,3-dimethylbutyl-thiacyclopentanium trifluoromethanesulfonate represented by the following formula was synthesized.

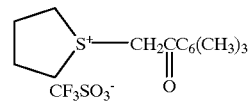

The following synthesis operation was carried out under a yellow lamp.

In a 300 ml three-necked flask, 2 g of 2-oxo-3,3-dimethylbutyl-thiacyclopentanium bromide obtained in Example 1 was dissolved in 20 ml of acetonitrile. To the solution, a solution prepared by dissolving 1.69 g of a potassium trifluoromethanesulfonate salt in 50 ml of acetonitrile was added dropwise. After stirring for three hours, the deposited potassium bromide was removed by filtration and acetonitrile was distilled off under reduced pressure by an evaporator. The residue was dissolved in chloroform and the insoluble matter was removed by filtration. Chloroform in the filtrate was distilled off under reduced pressure to obtain a transparent viscous liquid. To the transparent viscous liquid, 5 ml of acetone was added and the solution was added dropwise to 300 ml of diethyl ether. The deposited white crystal was collected by filtration and then recrystallized from ethyl acetate. The resulting white powder was dried under reduced pressure at 30° C. for six hours to obtain 2.21 g of 2-oxo-3,3-dimethylbutyl-thiacyclopentanium trifluoromethanesulfonate (yield: 87.7%).

The NMR analysis results of the resulting synthesized material are as follows. $^1$H-NMR (CDCl$_3$, internal standard: tetramethylsilane): δ (ppm) 1.23–1.27 (t, 9H, —CH$_3$), 2.23–2.31 (m, 2H, —CH$_2$—), 2.45–2.50 (m, 2H, —CH$_2$—), 3.46–3.50 (m, 2H, S$^+$—CH$_2$—), 3.63–3.70 (m, 2H, S$^+$—CH$_2$—), 4.97 (s, 2H, S$^+$—CH$_2$—C(O)—).

The elemental analysis results are as follows (the following theoretical value shows a calculated value to C$_{11}$H$_{19}$F$_3$O$_4$S$_2$ (MW336.38)).

Elemental Analysis

|  | C | H | S |
|---|---|---|---|
| Found value (% by weight) | 39.30 | 5.55 | 18.98 |
| Theoretical value (% by weight) | 39.28 | 5.69 | 19.06 |

The heat decomposition point was 113.5° C.

Example 10

2-oxo-3,3-dimethylbutyl-thiacyclopentanium nonafluorobutanesulfonate represented by the following formula was synthesized.

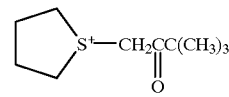

The following synthesis operation was carried out under a yellow lamp.

In the same manner as in Example 2, except that 3.03 g of a potassium nonafluorobutanesulfonate salt was used in place of the potassium trifluoromethanesulfonate salt, the synthesis test of 2-oxo-3,3-dimethylbutyl-thiacyclopentanium nonafluorobutanesulfonate was conducted. As a result, 1.91 g of 2-oxo-3,3-dimethylbutyl-thiacyclopentanium nonafluorobutanesulfonate was obtained (yield: 52%).

The NMR analysis results of the resulting synthesized material are as follows. $^1$H-NMR (CDCl$_3$, internal standard: tetramethylsilane): δ (ppm) 1.23–1.27 (t, 9H, —CH$_3$), 2.23–2.31 (m, 2H, —CH$_2$—), 2.45–2.50 (m, 2H, —CH$_2$—), 3.46–3.50 (m, 2H, S$^+$—CH$_2$—), 3.63–3.70 (m, 2H, S$^+$—CH$_2$—), 4.97 (s, 2H, S$^+$—CH$_2$—C(O)—).

Example 11

2-oxocyclohexyl-thiacyclopentanium trifluoromethanesulfonate represented by the following formula was synthesized.

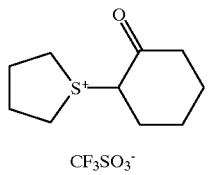

CF$_3$SO$_3^-$

The following synthesis operation was carried out under a yellow lamp.

In a 300 ml three-necked flask, 4 g of tetrahydrothiophene was dissolved in 40 ml of acetonitrile. To the solution, 6 g of 1-bromo-2-cyclohexanone was added dropwise while stirring. After stirring for three days, 100 ml of ether was added and the solution was ice-cooled to 0° C. After stirring for three hours, the deposited white crystal was collected by filtration. The white crystal was washed with ether and dried by a vacuum drier at 30° C. for four hours. In a 200 ml Kjeldahl flask, 2 g of the white crystal was dissolved in 20 ml of acetonitrile and then 100 ml of an acetonitrile solution of 1.46 g of a potassium trifluoromethanesulfonate salt was added dropwise. After stirring for three hours, the deposited potassium bromide was removed by filtration and acetonitrile was distilled off under reduced pressure by an evaporator. The residue was dissolved in chloroform and the insoluble matter was removed by filtration. Chloroform in the filtrate was distilled off under reduced pressure and the residue (transparent viscous liquid) was cooled in a refrigerator at −20° C. for three hours. The transparent viscous liquid was converted into a white crystal by cooling. The white crystal was recrystallized from ethyl acetate and then dried under reduced pressure at 30° C. for six hours to obtain 1.92 g of 2-oxocyclohexyl-thiacyclopentanium trifluoromethanesulfonate (yield: 75.4%).

The NMR analysis results of the resulting synthesized material are as follows. $^1$H-NMR (CDCl$_3$, internal standard: tetramethylsilane): δ (ppm) 1.04–1.11 (t, 3H, —CH$_3$), 1.82–1.92 (m, 4H, —CH$_2$—), 2.14–2.16 (m, 2H, —CH$_2$—), 2.65–2.70 (m, 2H, —CH$_2$—), 3.42–3.46 (m, 2H, S$^+$—CH$_2$—), 3.42–3.46 (m, 2H, S$^+$—CH$_2$—), 3.56–3.59 (m, 2H, S$^+$—CH$_2$—), 4.89 (s, 1H, S$^+$—CH$_2$—C(O)—).

The elemental analysis results are as follows [the following theoretical value shows a calculated value to C$_{10}$H$_{17}$F$_3$O$_4$S$_2$ (MW322.35)].

Elemental Analysis

|  | C | H | S |
|---|---|---|---|
| Found value (% by weight) | 47.26 | 5.32 | 19.89 |
| Theoretical value (% by weight) | 47.26 | 5.40 | 19.99 |

Example 12

Metyl-3-oxothiacyclopentanium trifluoromethanesulfonate represented by the following formula was synthesized.

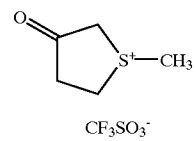

CF$_3$SO$_3^-$

The following synthesis operation was carried out under a yellow lamp.

In a 200 ml three-necked flask, 1 g of tetrahydrothiophen-3-one was dissolved in 20 ml of acetone. To the solution, 1.32 g of iodomethane was added dropwise while stirring. After stirring for one hour, 10 ml of an acetonitrile solution of 2.38 g of silver trifluoromethanesulfonate was added dropwise. After stirring for 24 hours, the deposited silver iodide was removed by filtration and acetonitrile was distilled off under reduced pressure by an evaporator. To the residue, 5 ml of acetone was added and the solution was added dropwise in 200 ml of diethyl ether. The resulting white powder was dried under reduced pressure at 630° C. for six hours to obtain 2.3 g of Metyl-3-oxothiacyclopentanium trifluoromethanesulfonate (yield: 93%).

The elemental analysis results are as follows [the following theoretical value shows a calculated value to C$_6$H$_9$F$_3$O$_4$S$_2$ (MW266.25)].

Elemental Analysis

|  | C | H | S |
|---|---|---|---|
| Found value (% by weight) | 35.00 | 4.90 | 20.80 |
| Theoretical value (% by weight) | 27.07 | 3.41 | 24.08 |

The melting point was 62.3° C.

Experiment 1

Measurement of Absorption of Alkylsulfonium Salt

Each of the sulfonium salts obtained in Examples 1 to 10 and 3.1 mg of triphenylsulfonium sulfonate (TPS105, manufactured by Midori Chemicals Co., Ltd.) were dissolved in 25 ml of acetonitrile and an ultraviolet absorption spectrum of the resulting solution was measured by using an ultraviolet-visible spectrometer (UV-365, manufactured by Shimadzu Corp.). The molar absorption coefficient to 193.4 nm (light of ArF excimer laser) is shown in Table 1 below.

TABLE 1

| | Molar absorption coefficient to 193.4 nm ($1 \cdot mol^{-1} \cdot cm^{-1}$) |
|---|---|
| Sulfonium salt obtained in Example 1 | 483.5 |
| Sulfonium salt obtained in Example 2 | 445.3 |
| Sulfonium salt obtained in Example 3 | 359.5 |
| Sulfonium salt obtained in Example 4 | 425.5 |
| Sulfonium salt obtained in Example 5 | 443.7 |
| Sulfonium salt obtained in Example 6 | 443.7 |
| Sulfonium salt obtained in Example 7 | 643.5 |
| Sulfonium salt obtained in Example 8 | 569.6 |
| Sulfonium salt obtained in Example 9 | 548.2 |
| Sulfonium salt obtained in Example 10 | 756.2 |
| Triphenylsulfonium triphenylsulfonate (TPS) | 54230 |

As a result, the following became apparent. That is, triphenylsulfonium trifluoromethanesulfonate (TPS) had strongly absorbed the light of ArF excimer laser and drastically lower the transparency of a resist when using as a photo acid generator for ArF resist. On the other hand, any of the sulfonium salt compounds of the present invention obtained in Examples 1 to 10 are suited for use as a constituent component of the resist for ArF excimer laser lithography because of its lower light absorption of the light of ArF excimer laser and excellent transparency to exposure light.

Experiment 2

Measurement of Transmittance of Alkylsulfonium Salt-Containing Resin Film 1.5 g of polymethyl methacrylate (PMMA) and the sulfonium salts obtained in Examples 2 and 6 were dissolved in ethyl lactate and, after filtering through a membrane filter, the resulting solution was rotationally coated on a 3 inch quartz substrate and then heated on a hot plate at 120° C. for 60 seconds. This operation gave a resin film of about 0.5 μm in thickness. The transmittance at 193.4 nm of the resulting film was measured by using an ultraviolet-visible spectrometer (UV-36). For comparison, the transmittance of a resin film containing triphenylsulfonium trifluoromethanesulfonate (TPS) or phenancylthiacyclopentanium trifluoromethanesulfonate (PTP) having a benzene ring was measured.

The measurement results are shown in FIG. 1. The sulfonium salts obtained in Examples 2 and 6 did not lower the transmittance of the resin film. On the other hand, the transmittance was drastically lowered with the increase of the content of triphenylsulfonium trifluoromethanesulfonate or phenancylthiacyclopentanium trifluoromethanesulfonate.

Experiment 3

Evaluation of Heat Stability in Resin Film

The poly(methyl methacrylate$_{40}$-tertiary butyl methacrylate$_{40}$-methacrylic acid$_2$) film (film thickness: 0.4 μm) containing 1% by weight of the sulfonium salt compounds obtained in Examples 2, 3, 6 and 7 were heated on a hot plate at a predetermined temperature for 60 seconds. And those were cooled immediately to room temperature and then dipped in a developer (2.38% by weight of tetramethylammonium hydroxide (aqueous TMAH solution)) for 60 seconds.

In case the sulfonium compound is thermally decomposed, the acid decomposes a protective group (tertiary butyl group) of the resin, thereby enabling the resin to become insoluble in the developer. Therefore, the heating temperature at which the resin film was dissolved in the developer is taken as a heat decomposition point of the sulfonium salt compound in the resin film.

As a result, any of the heat decomposition point of the sulfonium salt compounds obtained in Examples 2, 3, 6 and 7 in the resin film was 170° C. or higher and was 47–53° C. higher than that of 2-oxocyclohexylmethyl(2-norbornyl) sulfonium triflate. Therefore, of the sulfonium salt compounds were superior in heat stability.

TABLE 2

| Sulfonium salt compound | Decomposition initiation point |
|---|---|
| Compound obtained in Example 2 | 178° C. |
| Compound obtained in Example 3 | 174° C. |
| Compound obtained in Example 6 | 172° C. |
| Compound obtained in Example 7 | 172° C. |
| β-oxycyclohexyl-methyl(2-norbornyl) sulfonium triflate | 125° C. |

Experiment 4

Exposure Test Using ArF Excimer Laser

The ArF excimer laser contact exposure test using the photoresist composition of the present invention was conducted.

The following test was conducted under a yellow lamp.

First, a resist composition was prepared in accordance with the following formulation:

(a) a resin having the following structure: 2.85 g,

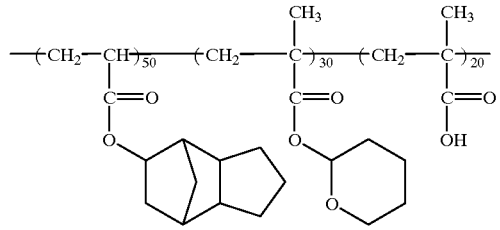

(b) 2-oxobutyl-thiacyclohexanium trifluoromethanesulfonate (photo acid generator: compound obtained in Example 2): 0.15 g, and (c) ethyl lactate (solvent): 15 g.

The above mixture was filtered through a 0.2 μm Teflon filter to prepare a resist. The resist material was spin coated on a 4 inch silicon wafer, and then baked on a hot plate at 120° C. for 60 seconds to form a thin film having a thickness of 0.4 μm. The film was exposed to light of ArF excimer laser by means of an ArF excimer stepper (NA=0.55) through a mask. Immediately after the exposure, the film was baked on a hot plate at 130° C. for 60 seconds, developed with an alkali developer (aqueous solution of 0.05% by weight of tetramethylammonium hydroxide) at a liquid temperature of 23° C. for 60 seconds, and then rinsed with pure water for 60 seconds.

As a result, only the exposed portion was removed by dissolving in the developer to obtain a positive pattern. When the exposure energy is 40.5 mJ/cm$^2$ in this test, the definition with a line-and-space of 0.20 μm was obtained.

Experiment 5

Exposure Test Using ArF Excimer Laser

In the same manner as in Experiment 3, except that the photo acid generator shown in Table 2 was used in place of 2-oxobutyl-thiacyclohexanium trifluoromethanesulfonate, a photoresist composition was prepared. Using the resulting photoresist composition, contact exposure was conducted. The resulting resolution and sensitivity are shown in Table 3.

TABLE 3

|  | Resolution ($\mu$mL/S) | Sensitivity (mJ/cm$^2$) |
| --- | --- | --- |
| Resist using sulfonium salt obtained in Example 3 | 0.225 | 52.6 |
| Resist using sulfonium salt obtained in Example 4 | 0.25 | 66.5 |
| Resist using sulfonium salt obtained in Example 6 | 0.21 | 9.2 |
| Resist using sulfonium salt obtained in Example 7 | 0.20 | 27.3 |
| Resist using sulfonium salt obtained in Example 9 | 0.21 | 12.5 |
| Resist using TPS | 0.3 | 1.5 |

As a result, excellent resolution and sensitivity could be exhibited when using photoresist compositions containing the sulfonium salt compounds obtained in Examples 3, 4, 6, 7 and 9, whereas, the resolution was poor when using a photoresist composition containing TPS.

Experiment 6

Exposure Test Using ArF Excimer Laser

The ArF excimer laser contact exposure test using the photoresist composition of the present invention was conducted.

The following test was conducted under a yellow lamp.

First, a resist composition was prepared in accordance with the following formulation:

(a) a resin having the following structure: 2.4 g,

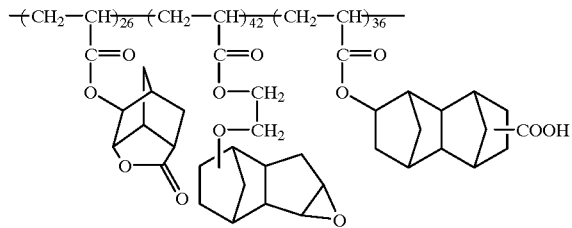

(b) cyclohexyl(2-oxocyclohexyl)(2-oxobutyl)sulfonium trifluoromethanesulfonate (photo acid generator: compound obtained in Example 1): 0.15 g,
(c) a crosslinking agent (2,3-dihydroxy-5-hydroxymethylnorbornene): 0.45 g, and
(d) ethyl lactate (solvent): 11.5 g.

The above mixture was filtered through a 0.2 $\mu$m Teflon filter to prepare a resist. The resist material was spin coated on a 4 inch silicon wafer, and then baked on a hot plate at 130° C. for 60 seconds to form a thin film having a thickness of 0.4 $\mu$m. The film was exposed to light of ArF excimer laser by means of an ArF excimer stepper (NA=0.55) through a mask. Immediately after the exposure, the film was baked on a hot plate at 140° C. for 60 seconds, developed with an aqueous solution of 2.38% by weight of tetramethylammonium hydroxide at a liquid temperature of 23° C. for 60 seconds, and then rinsed with pure water for 60 seconds.

As a result, only the unexposed portion was removed by dissolving in the developer to obtain a negative pattern. When the exposure energy is 11.8 mJ/cm$^2$ in this test, a line of 0.20 $\mu$m was resolved.

What is claimed is:

1. A positive photoresist composition comprising a photo acid generator comprising a sulfonium salt compound represented by the following general formula (1)

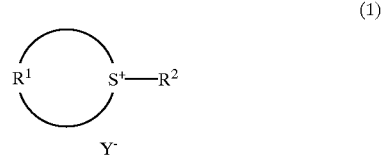

wherein $R^1$ represents an alkylene group, or an alkylene group having an oxo group, $R^2$ represents a straight-chain, branched-chain, monocyclic, polycyclic or bridged cyclic alkyl group having an oxo group, or a straight-chain, branched-chain, monocyclic, polycyclic or bridged cyclic alkyl group, provided that either of $R^1$ and $R^2$ has an oxo group, and $Y^-$ represents a counter ion.

2. A positive photoresist composition according to claim 1, wherein said photo acid generator comprises a sulfonium salt compound of the general formula (1) wherein $R^1$ represents an alkylene group having 4 to 7 carbon atoms, or an alkylene group having an oxo group, and $R^2$ represents a straight-chain, branched-chain, monocyclic, polycyclic or bridged cyclic alkyl group having an oxo group, which has 3 to 12 carbon atoms, or a straight-chain, branched-chain, monocyclic, polycyclic or bridged cyclic alkyl group having 3 to 12 carbon atoms.

3. A positive photoresist composition according to claim 1, wherein said photo acid generator comprises a sulfonium salt compound of the general formula (1) wherein $R^1$ represents an alkylene group having 4 to 7 carbon atoms, or a 2-oxoalkylene group having 4 to 7 carbon atoms, and $R^2$ represents a straight-chain, branched-chain, moncyclic, polycyclic or bridged cyclic 2-oxoalkyl group having 3 to 12 carbon atoms, or a straight-chain, branched-chain, monocyclic, polycyclic or bridged cyclic alkyl group having 3 to 12 carbon atoms.

4. A positive photoresist composition according to claim 1, wherein said photo acid generator comprises a sulfonium salt compound of the general formula (1) wherein the counter ion represented by $Y^-$ is $Z-SO_3^-$ [in which Z is $C_nF_{2n+1}$ (n is any one of 1 to 8), an alkyl group, or an alkyl-substituted or non-substituted aromatic group], $BF_4^-$, $AsF_6^-$, $SbF_6^-$, $ClO_4^-$, $Br^-$, $Cl^-$, or $I^-$.

5. A negative photoresist composition comprising a photo acid generator comprising a sulfonium salt compound represented by the following general formula (1)

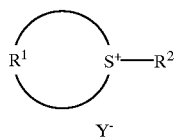

(1)

wherein R¹ represents an alkylene group, or an alkylene group having an oxo group, R² represents a straight-chain, branched-chain, monocyclic, polycyclic or bridged cyclic alkyl group having an oxo group, or a straight-chain, branched-chain, monocyclic, polycyclic or bridged cyclic alkyl group, provided that either of R¹ and R² has an oxo group, and Y⁻ represents a counter ion.

6. A negative photoresist composition according to claim 5, wherein said photo acid generator comprises a sulfonium salt compound of the general formula (1) wherein R¹ represents an alkylene group having 4 to 7 carbon atoms, or an alkylene group having an oxo group, and R² represents a straight-chain, branched-chain, monocyclic, polycyclic or bridged cyclic alkyl group having an oxo group, which has 3 to 12 carbon atoms, or a straight-chain, branched-chain, monocyclic, polycyclic or bridged cyclic alkyl group having 3 to 12 carbon atoms.

7. A negative photoresist composition according to claim 5, wherein said photo acid generator comprises a sulfonium salt compound of the general formula (1) wherein R¹ represents an alkylene group having 4 to 7 carbon atoms, or a 2-oxoalkylene group having 4 to 7 carbon atoms, and R² represents a straight-chain, branched-chain, monocyclic, polycyclic or bridged cyclic 2-oxoalkyl group having 3 to 12 carbon atoms, or a straight-chain, branched-chain, monocyclic, polycyclic or bridged cyclic alkyl group having 3 to 12 carbon atoms.

8. A negative photoresist composition according to claim 5, wherein said photo acid generator comprises a sulfonium salt compound of the general formula (1) wherein the counter ion represented by Y⁻ is Z—SO₃⁻ [in which Z is $C_nF_{2n+1}$ (n is any one of 1 to 8), an alkyl group, or an alkyl-substituted or non-substituted aromatic group], $BF_4^-$, $AsF_6^-$, $SbF_6^-$, $ClO_4^-$, $Br^-$, $Cl^-$, or $I^-$.

9. A pattern forming method, which comprises forming a thin film on a substrate using the photoresist composition of claim 5, exposing to light having a wavelength of 300 nm or less, and developing to form a pattern.

10. A pattern forming method according to claim 9, wherein the exposure light is light of an ArF excimer laser.

11. A pattern forming method according to claim 9, wherein the exposure light is light of $F_2$ excimer laser.

12. A pattern forming method, which comprises forming a thin film on a substrate using the photoresist composition of claim 5, exposing to light having a wavelength of 300 nm or less, and developing to form a pattern.

13. A pattern forming method according to claim 12, wherein the exposure light is light of ArF excimer laser.

14. A pattern forming method according to claim 12, wherein the exposure light is light of $F_2$ excimer laser.

* * * * *